United States Patent [19]
Majeed et al.

[11] Patent Number: 6,054,585
[45] Date of Patent: Apr. 25, 2000

[54] PROCESS FOR MAKING HIGH PURITY PIPERINE FOR NUTRITIONAL USE

[75] Inventors: Muhammed Majeed; Vladimir Badmaev, both of Piscataway, N.J.

[73] Assignee: Sabinsa Corporation, Piscataway, N.J.

[21] Appl. No.: 09/219,512

[22] Filed: Dec. 23, 1998

[51] Int. Cl.$^7$ .................................................. C07D 407/06
[52] U.S. Cl. .......................................... 546/197; 514/321
[58] Field of Search ............................... 546/197; 514/321

[56] References Cited

U.S. PATENT DOCUMENTS

| | | | |
|---|---|---|---|
| 3,619,212 | 11/1971 | Mori et al. | 426/651 |
| 4,409,257 | 10/1983 | Deline | 426/651 |
| 5,087,458 | 2/1992 | Witkewitz et al. | 426/3 |
| 5,536,506 | 7/1996 | Majeed et al. | 424/464 |
| 5,616,593 | 4/1997 | Patel | 514/321 |
| 5,744,161 | 4/1998 | Majeed et al. | 424/464 |

OTHER PUBLICATIONS

Windholz et al. Merck Index, 9th ed. p. 972, 1976.
Graham Reaction of Piperine with nitric acid. J. Phar. Sci. v. 54 (2) p. 319–321, Feb. 1965.
Tabuneng et al. "Studies on the constituents of the crude drug piperis longi fructus" Chem. Phar. Bull. vo. 31 (10) p. 3562–65, Oct. 1983.

*Primary Examiner*—Ceila Chang
*Attorney, Agent, or Firm*—Arent Fox Kintner Plotkin & Kahn, PLLC

[57] ABSTRACT

The present invention relates to a process of making high purity piperine for nutritional and nutraceutical application. This process recovers piperine from piperine-containing oleoresin by using isourea, urea or a urea derivative to remove organic matter other than piperine from the oleoresin. Preferably, the process recovers piperine from oleoresin of fruit of piper nigrum or piper longum. More preferably, the process recovers piperine from oleoresin of fruit of piper nigrum, i.e. black pepper.

36 Claims, No Drawings

PROCESS FOR MAKING HIGH PURITY PIPERINE FOR NUTRITIONAL USE

BACKGROUND OF THE INVENTION

1. Field of the Invention

The present invention relates to a process for making high purity piperine by removing impurities from oleoresin of the fruit or the plant of the Piperaceae family or any other natural source of alkaloid piperine. Piperine is useful for enhancing the bioavailability of nutritional and/or botanical compounds.

The fifty percent increase in life expectancy of Americans from 1930 to 1980 can, in part, be attributed to the improvement in nutrition in the United States during that period. However, the situation today remains far from ideal, since six out of ten of the leading causes of death in this country, including heart attack, cancer, cirrhosis of the liver, and diabetes, are linked to diet. It becomes increasingly obvious that many of those diseases could be prevented with a well balanced diet and efficient nutritional supplementation with certain vitamins and minerals.

The problem is particularly severe in older Americans. Approximately 30 percent of older Americans do not get the dietary requirements of all the essential nutrients. The hazards of food-drug interactions in depleting essential nutrients are well recognized. It is unavoidable that old age calls for increased use of medications. For example, use of certain antibiotics decreases absorption of calcium and iron, while EDTA chelation therapy decreases absorption of zinc, iron, copper, and magnesium.

In addition, many foods which increase the risk of cancer and cardiovascular disease have to be eliminated from the diet, which further depletes the sources of essential nutrients. For example, excellent sources of vitamin B and vitamin D, such as red meat, liver, egg yolk, cheese and dairy products, are often limited because of their high cholesterol content.

Limited menu also causes a depletion of essential amino acids, such as tryptophan, which is important precursor of neurotransmitters, and may play a role in the prevention of brain deterioration with aging.

The availability of essential nutrients is further compromised by poor gastrointestinal absorption, which deteriorates with the advancing age.

The traditional way to offset insufficient nutrient supplementation, insufficient gastrointestinal absorption and insufficient metabolic utilization of essential nutrients is to administer large doses of compensating materials, such as vitamin and mineral supplements.

The present invention provides an alternative method for improving nutritional status by providing high purity piperine which increases the bioavailability of various nutritional materials.

The bioavailability of nutrients is also relevant to animal health as well as human health. Thus, the process of the present invention is also intended to provide piperine be used in veterinary practice.

2. Description of Related Art

Piperine, or mixtures containing piperine, have been shown to increase the bioavailability of nutritional and/or botanical compounds (Majeed et al. (1996), U.S. Pat. No. 5,536,506; Majeed et al. (1998), U.S. Pat. No. 5,744,161). The prior art process of U.S. Pat. No. 5,744,161 isolates piperine from a suitable oleoresin material obtained from the fruit or plant of the Piperaceae family. In contrast, the present invention discloses a process of obtaining piperine by removing organic matter (impurities) other than piperine from the oleoresin obtained from the fruit or plant of the Piperaceae family or other natural source of alkaloid piperine, leaving behind piperine at a high purity. The removal process is achieved by using isourea, urea or a urea derivative. By first removing the impurities instead of isolating piperine, the process of the present invention unexpectedly results in a higher yield of piperine than the prior art process. Compared with the process of the prior art, the process of the present invention also has an additional advantage of providing piperine of higher purity. Thus, the biological activity of piperine obtained by the process of the present invention is more specific than piperine obtained by the prior art process.

SUMMARY OF THE INVENTION

The present invention is directed to a process of making high purity piperine. Piperine may be obtained by a novel process of the present invention by recovering piperine from the oleoresin of the plant of such as, but not limited to, Piperaceae family, e.g. fruits of piper nigrum or piper longum, of the Piperaceae family. The novel process can produce piperine of a purity of at least 10% by weight.

In accordance with the present invention, there is provided a novel process of recovering piperine from the oleoresin of the fruit of Piperaceae, such as piper nigrum and piper longum, by removal of impurities from the oleoresin. Rather than extracting piperine from the oleoresin leaving behind the impurities, as taught by the prior art, the novel process of the present invention removes the impurities in order to obtain piperine at a yield of piperine recovery of 15–40% higher than prior art processes. One embodiment of the novel process comprises the following steps:

(1) mixing isourea or $R^1R^2NC(O)NR^3R^4$, an organic solvent and piperine-containing oleoresin of any part of a plant from the Piperaceae family or any other plant containing alkaloid piperine to form a mixture, wherein $R^1$, $R^2$, $R^3$ and $R^4$ are independently H, a $C_1$–$C_6$ aliphatic radical or a phenyl radical; and thereafter (2) removing impurities and the solvent from the mixture to provide piperine at a purity of at least 10% by weight.

Within the scope of the present invention is another embodiment of the process for obtaining piperine, which process comprises the following steps:

(1) mixing isourea or $R^1R^2NC(O)NR^3R^4$ and an organic solvent to form a first mixture, wherein $R^1$, $R^2$, $R^3$ and $R^4$ are independently H, a $C_1$–$C_6$ aliphatic radical or a phenyl radical;

(2) mixing the first mixture and piperine-containing oleoresin of any part of a plant from the Piperaceae family or any other plant containing alkaloid piperine to form a second mixture; and thereafter (3) removing impurities and the solvent from the second mixture to provide piperine.

Also within the scope of the present invention is another embodiment of the process for obtaining piperine, comprising the following steps:

(1) mixing isourea or $R^1R^2NC(O)NR^3R^4$ and an organic solvent to form a first mixture, wherein $R^1$, $R^2$, $R^3$ and $R^4$ are independently H, a $C_1$–$C_6$ aliphatic radical or a phenyl radical;

(2) mixing the first mixture and piperine-containing oleoresin of any part of a plant from the Piperaceae family or any other plant containing alkaloid piperine to form a second mixture;

(3) heating the second mixture to obtain a heated second mixture;

(4) cooling the heated second mixture to form a cooled second mixture;

(5) removing impurities from the cooled second mixture to obtain a piperine solution; and thereafter (6) removing said organic solvent from the piperine solution to recover piperine.

Optionally, after step (1) and before step (2), the first mixture is heated before being mixed with the oleoresin to form the second mixture.

DETAILED DESCRIPTION OF THE INVENTION

The conditions, reactants and reagents for the piperine-recovery process of the present invention disclosed above are further discussed herein. The $C_1$–$C_6$ aliphatic radical is any saturated or unsaturated, straight or branched chain hydrocarbon radical having one to six carbon atoms. Examples of the $C_1$–$C_6$ aliphatic radical include $C_1$–$C_6$ alkyl, $C_1$–$C_6$ alkenyl or $C_1$–$C_6$ alkynyl radicals. Examples of $R^1R^2NC(O)NR^3R^4$ include urea, methylurea, N,N-dimethylurea, N,N'-dimethylurea, ethylurea, N-ethyl-N-methylurea, N-ethyl-N'-methylurea, N,N-diethylurea, N,N'-diethylurea, propylurea, ethenylurea, 1-propenylurea, 2-propenylurea and ethynylurea. Preferably, $R^1R^2NC(O)NR^3R^4$ is urea, methylurea, N,N-dimethylurea, N,N'-dimethylurea and ethyl urea. More preferably, $R^1R^2NC(O)NR^3R^4$ is urea.

The organic solvent can be any protic organic solvent. Preferably, the organic solvent is $R^5OH$ or $R^6COOH$, with $R^5$ and $R^6$ independently being a $C_1$–$C_6$ aliphatic radical, e.g. a $C_1$–$C_6$ alkyl, $C_1$–$C_6$ alkenyl or $C_1$–$C_6$ alkynyl radical, wherein the $C_1$–$C_6$ aliphatic radical is optionally halogenated. Examples of the organic solvent include methanol, ethanol, propanol, isopropanol, butanol, isobutanol, t-butanol, acetic acid and trifluoroacetic acid, with methanol, ethanol, butanol and acetic acid being preferred. More preferably, the organic solvent is ethanol.

The piperine-recovery process of the present invention uses isourea, urea or a urea derivative as a clathrate compound, i.e., a compound to separate pure piperine from other organic compounds, e.g. fatty acids, mono-, di-, triglycerides, choline, lecithin, waxes and squalenes, in the oleoresin of the fruit of Piperaceae, such as piper nigrum and piper longum. Among sources of alkaloid piperine, the fruits of piper nigrum, i.e. black pepper, and piper longum, i.e. long pepper, are preferred. The fruit of piper nigrum is more preferred.

The optional heating of the first mixture of isourea, urea or the urea derivative and the organic solvent is preferably carried out at a temperature of about 30° to about 95° C. More preferably, the first mixture is heated at a temperature of about 42° to about 85° C. or until a clear solution is obtained. The heating of the first mixture can be conducted in an incubator. To form the second mixture in the piperine-recovery process, the first mixture of isourea, urea or the urea derivative and the organic solvent is mixed with the oleoresin in the following range of proportions: about 5–25 parts of isourea, urea or the urea derivative: about 10–75 parts of the organic solvent: about 1 part of oleoresin.

The second mixture is heated preferably at a temperature of about 30° to about 95° C. More preferably, the second mixture is heated at a temperature of about 42° to about 85° C. Alternatively, the second mixture is heated to reflux. The second mixture is preferably heated for at least 10 minutes (more preferably about 30 minutes to about an hour).

The heated second mixture is then preferably cooled to less than about 10° C. to terminate the formation of the clatharate compound. More preferably, the heated second mixture is cooled to about 0° C.–5° C. (0° is much preferred) to terminate the formation of the clatharate compound. The organic impurities in the form of the urea complex are preferably filtered out of the cooled incubated second mixture to obtain the piperine solution in the organic solvent. The organic solvent can then be removed by any known process for removing a solvent from a solution. For instance, the organic solvent can be removed by evaporation under heating.

Another aspect of the present invention is another embodiment of the process for obtaining piperine, comprising the following steps:

(1) mixing about 5–25 parts of urea and about 10–75 parts of methanol to form a first mixture;

(2) heating said first mixture at a temperature of about 42° to about 85° C. to obtain a clear heated first mixture;

(3) mixing the heated first mixture and piperine-containing oleoresin of the fruit of black pepper to form a second mixture;

(4) heating the second mixture at a temperature of about 42° to about 85° C. for about 30 minutes to obtain a heated second mixture;

(5) cooling the heated second mixture at a temperature of about 0° C. to form a cooled second mixture;

(6) removing impurities from the cooled second mixture by filtration to obtain a piperine solution; and thereafter (7) heating the piperine solution to remove methanol from the piperine solution to recover piperine.

Piperine made by the novel process of the present invention is useful in enhancing the bioavailability of nutrients and/or botanical compounds. As a daily supplement taken with a nutrient or nutrients by an average healthy adult, piperine is effective and safe in a broad dose range. A preferred effective dose range of piperine for oral use to enhance nutrient bioavailability is 0.0004–0.15 mg/kg/day. The recommended dose of piperine for a healthy individual for oral use is approximately 5 mg/person/day. The recommended dose in cases of clinically diagnosed nutritional deficiencies is up to 15 mg/person/day in divided doses, i.e., 5 mg every six hours (in the morning, at noon, and in the evening). When used as a preparation for topical or parenteral use to improve crossing over through a biological barrier, the compositions of the present invention contain, as an essential ingredient, 0.00004–0.015 mg/kg of body weight of piperine. The nutritional materials are used in nutritionally effective amounts.

Black pepper contains approximately 5–9% piperine and is listed by the FDA as an herb which is generally recognized as safe (GRAS) for its intended use as spice, seasoning, or flavoring. The bioenhancing dose of piperine as used in the present invention is a maximum of approximately 15 mg/person/day, or no more than 20 mg/day.

The following examples are not intended to be limiting in any way, but demonstrate an embodiment of the present invention.

EXAMPLES

Comparative Example

A process disclosed in U.S. Pat. No. 5,744,161.

Commercially available Black pepper oleoresin or Long pepper oleoresin is used as the source of piperine. Ground up Black pepper or Long pepper can also be used.

To a mixture of butanol and hexane (35 liters), 35 kg Black pepper oleoresin is added and heated to 40° C. The mixture is then cooled and filtered.

The precipitate is washed with Butanol/hexane mixture to obtain crude piperine.

The crude piperine is dissolved in ethanol at 60° C. and treated with alumina and charcoal by stirring. It is then filtered and concentrated under vacuum to obtain a powder.

Bioperine®

Material thus prepared has the following specifications:
Color: Pale yellow crystalline powder
Melting range: 128 degrees–131 degrees Celsius
Assay: min. 98% pure piperine (by HPLC)

Example

A process to recover piperine from resin of black pepper.

A reaction vessel was charged with 0.9 kg of urea, 3.7 kg of ethanol or 2.7 kg of methanol and 0.3 kg of the resin of black pepper to form a mixture. The mixture was refluxed for approximately one hour. The refluxed mixture was cooled overnight to a temperature of 0° to 5° C. The cooled mixture was then filtered to remove solids (e.g. wax, urea, fatty acids). The filtrate was then concentrated to obtain 180 g of piperine and some unreacted urea. The 180 g of piperine was recrystallized by adding ethanol. The piperine crystals were collected by filtration and dried to yield approximately 75 g of 98% pure piperine.

We claim:

1. A process for obtaining piperine, comprising the following steps:
    (1) mixing isourea or $R^1R^2NC(O)NR^3R^4$, an organic solvent and piperine-containing oleoresin from a source to form a mixture A, wherein $R^1$, $R^2$, $R^3$ and $R^4$ are independently H, a $C_1$–$C_6$ aliphatic radical or a phenyl radical, wherein said source is any part of a plant from family Piperaceae or any other plant containing alkaloid piperine; and thereafter
    (2) removing impurities and said organic solvent from the mixture A to provide piperine at a concentration of at least 10% by weight.

2. The process of claim 1, wherein in step (1), isourea or $R^1R^2NC(O)NR^3R^4$ is mixed with the organic solvent to form a first mixture, which first mixture is then mixed with said oleoresin to form the mixture A.

3. The process of claim 2, wherein in step (1), $R^1R^2NC(O)NR^3R^4$ is mixed with the organic solvent to form a first mixture, which first mixture is then mixed with said oleoresin to form the mixture A, wherein $R^1$, $R^2$, $R^3$ and $R^4$ are independently H, a $C_1$–$C_6$ alkyl, $C_1$–$C_6$ alkenyl or $C_1$–$C_6$ alkynyl radical.

4. The process of claim 3, wherein $R^1$, $R^2$, $R^3$ and $R^4$ are independently H, methyl or ethyl.

5. The process of claim 4, wherein $R^1$, $R^2$, $R^3$ and $R^4$ are H.

6. The process of claim 1, wherein the organic solvent is a protic organic solvent.

7. A process for obtaining piperine, comprising the following steps:
    (1) mixing isourea or $R^1R^2NC(O)NR^3R^4$ and an organic solvent to form a first mixture, wherein $R^1$, $R^2$, $R^3$ and $R^4$ are independently H, a $C_1$–$C_6$ aliphatic radical or a phenyl radical;
    (2) mixing the first mixture and piperine-containing oleoresin from a source to form a second mixture, wherein said source is any part of a plant from family Piperaceae or any other plant containing alkaloid piperine;
    (3) heating the second mixture to obtain a heated second mixture;
    (4) cooling the heated second mixture to form a cooled second mixture;
    (5) removing impurities from the cooled second mixture to obtain a piperine solution; and thereafter
    (6) removing said organic solvent from the piperine solution to recover piperine at a concentration of at least 10% by weight.

8. The process of claim 7, wherein the first mixture is heated before mixing with said oleoresin to form the second mixture in step (2).

9. The process of claim 7, wherein step (1) comprises mixing $R^1R^2NC(O)NR^3R^4$ and an organic solvent to form a first mixture, wherein $R^1$, $R^2$, $R^3$ and $R^4$ are independently H, a $C_1$–$C_6$ alkyl, $C_1$–$C_6$ alkenyl or $C_1$–$C_6$ alkynyl radical.

10. The process of claim 9, wherein $R^1$, $R^2$, $R^3$ and $R^4$ are independently H, methyl or ethyl.

11. The process of claim 10, wherein $R^1$, $R^2$, $R^3$ and $R^4$ are H.

12. The process of claim 7, wherein the organic solvent is a protic organic solvent.

13. The process of claim 12, wherein the organic solvent is $R^5OH$ or $R^6COOH$, with $R^5$ and $R^6$ independently being an optionally halogenated $C_1$–$C_6$ aliphatic radical.

14. The process of claim 13, wherein $R^5$ and $R^6$ are independently an optionally halogenated $C_1$–$C_6$ alkyl, $C_1$–$C_6$ alkenyl or $C_1$–$C_6$ alkynyl radical.

15. The process of claim 14, wherein the organic solvent is methanol, ethanol, propanol, isopropanol, butanol, isobutanol, t-butanol, acetic acid or trifluoroacetic acid.

16. The process of claim 15, wherein the organic solvent is methanol, ethanol, butanol or acetic acid.

17. The process of claim 16, wherein the organic solvent is ethanol.

18. The process of claim 9, wherein step (1) comprises mixing about 5–25 parts of $R^1R^2NC(O)NR^3R^4$ and about 10–75 parts of the organic solvent to form the first mixture.

19. The process of claim 7, wherein said source is the fruit of piper nigrum or piper longum.

20. The process of claim 19, wherein said source is the fruit of piper nigrum.

21. The process of claim 8, wherein the first mixture is heated at a temperature of about 30° to about 95° C. in step (2).

22. The process of claim 21, wherein the first mixture is heated at a temperature of about 42° to about 85° C. in step (2).

23. The process of claim 8, wherein the first mixture is heated until the first mixture becomes clear in step (2).

24. The process of claim 7, wherein the second mixture is heated in step (3) at a temperature of about 30° to about 95° C.

25. The process of claim 24, wherein the second mixture is heated at a temperature of about 42° to about 85° C.

26. The process of claim 25, wherein the second mixture is heated at a temperature of about 42° to about 85° C. for at least 10 minutes in step (3).

27. The process of claim 26, wherein the second mixture is heated at a temperature of about 42° to about 85° C. for about 30 minutes in step (3).

28. The process of claim 7, wherein the second mixture is heated to reflux in step (3).

29. The process of claim 28, wherein the second mixture is heated to reflux for about 1 hour in step (3).

30. The process of claim 7, wherein the heated second mixture is cooled at a temperature of less than about 10° C. in step (4).

31. The process of claim 30, wherein the heated second mixture is cooled at a temperature of about 0° C.–5° C. in step (4).

32. The process of claim 31, wherein the heated second mixture is cooled at a temperature of about 0° C. in step (4).

33. The process of claim 7, wherein the impurities are removed from the cooled second mixture by filtration in step (5).

34. The process of claim 7, wherein the organic solvent is removed by evaporation in step (6).

35. A process for obtaining piperine, comprising the following steps:
   (1) mixing about 5–25 parts of urea and about 10–75 parts of ethanol to form a first mixture;
   (2) heating said first mixture at a temperature of about 42° to about 85° C. to obtain a clear heated first mixture;
   (3) mixing the heated first mixture and piperine-containing oleoresin of the fruit of black pepper to form a second mixture;
   (4) heating the second mixture at a temperature of about 42° to about 85° C. to obtain a heated second mixture;
   (5) cooling the heated second mixture at a temperature of about 0° C. to form a cooled second mixture;
   (6) removing impurities from the cooled second mixture by filtration to obtain a piperine solution; and thereafter
   (7) heating the piperine solution to remove ethanol from the piperine solution to recover piperine at a concentration of at least 10% by weight.

36. The process of claim 1, wherein the organic solvent is ethanol, which is mixed with $R^1R^2NC(O)NR^3R^4$, with $R^1$, $R^2$, $R^3$ and $R^4$ being H, and the piperine-containing oleoresin of said source to form a mixture, which mixture is refluxed for approximately 1 hour and then cooled to a temperature of about 0°–5° C. to form mixture A in step (1), wherein said source is the fruit of black pepper; and wherein the impurities are removed from mixture A by filtration and ethanol is removed from mixture A by evaporation to provide piperine in step (2).

* * * * *